United States Patent [19]

Sinnreich

[11] 4,291,687
[45] Sep. 29, 1981

[54] INFLATABLE PACKING FOR SURGICAL USE HAVING AUXILIARY INTESTINAL SUPPORTING MEMBER

[76] Inventor: Manfred Sinnreich, 160 Ft. Hill Rd., Scarsdale, N.Y. 10583

[21] Appl. No.: 119,947

[22] Filed: Feb. 8, 1980

Related U.S. Application Data

[63] Continuation of Ser. No. 82,793, Mar. 2, 1978, abandoned.

[51] Int. Cl.³ .................. A61F 5/46; A61M 27/00
[52] U.S. Cl. ...................................... 128/129; 128/344
[58] Field of Search ............... 128/132, 129, 246, 325, 128/344, 349 B, 349 BV, 131, 1 R

[56] References Cited

U.S. PATENT DOCUMENTS

| | | | |
|---|---|---|---|
| 1,306,184 | 6/1919 | Jones | 128/246 X |
| 1,915,794 | 6/1933 | Leonhardt | 128/129 |
| 3,889,685 | 6/1975 | Miller et al. | 128/344 X |
| 3,896,816 | 7/1975 | Mattler | 128/246 X |

Primary Examiner—Lee S. Cohen
Assistant Examiner—Michael H. Thaler

[57] ABSTRACT

An inflatable surgical packing particularly suited for filling the body cavity formed after hysterectomies, and exenterations having an additional non-inflatable element on an inner axial end thereof extending transversely to support the loops of intestines and the omentum, and preventing pinching thereof between the device and a wall of the cavity, as well as serving to maintain the intestine clear of the raw surface of the cavity to safely permit the surface coating of the denuded area and the use of irradiation of the cavity following surgery.

1 Claim, 2 Drawing Figures

INFLATABLE PACKING FOR SURGICAL USE HAVING AUXILIARY INTESTINAL SUPPORTING MEMBER

RELATED APPLICATION

This application is a continuation of my co-pending application Ser. No. 82,793 filed Mar. 2, 1978, now abandoned under the same title.

BACKGROUND OF THE INVENTION

In my prior U.S. Pat. No. 3,918,431 dated Nov. 11, 1975, there is disclosed an inflatable device suitable for filling the void formed by the surgical removal of various organs, typically after hysterectomies and/or exenterations, and providing means for draining the cavity during the healing process. As the surface of the cavity slowly acquires surface coating, the device is progressively deflated, and ultimately withdrawn through the vagina. Inflation can be accomplished using either air or a fluid solution.

Since inflated devices of this type do not provide right angle edges to the wall of the cavity, particularly when less than fully inflated, there exists a tendency for the otherwise unsupported intestinal loops and/or omentum to fall in the areas adjacent the surfaces of the cavity, and become pinched between the wall and a surface of the inflated device, giving rise to the possibility of a traumatic condition, and, in extreme cases, the interference with normal functions. The support of the loops of intestines and/or omentum at the edges of the cavity also effectively promotes the often necessary postoperative step of irradiation without incurring postradiation effects to the intestines and/or omentum.

SUMMARY OF THE INVENTION

Briefly stated, the invention contemplates the provision of an additional, generally cup-like support member possessing a limited degree of rigidity and having a peripheral edge which seals the above-mentioned peripheral interstice, with the edge engaging the cavity wall. With full inflation of the inflatable element, the intestines and omentum are fully supported and maintained out of the area of the packing, wherein the above-mentioned disadvantages are substantially eliminated.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENT

Figure 1:
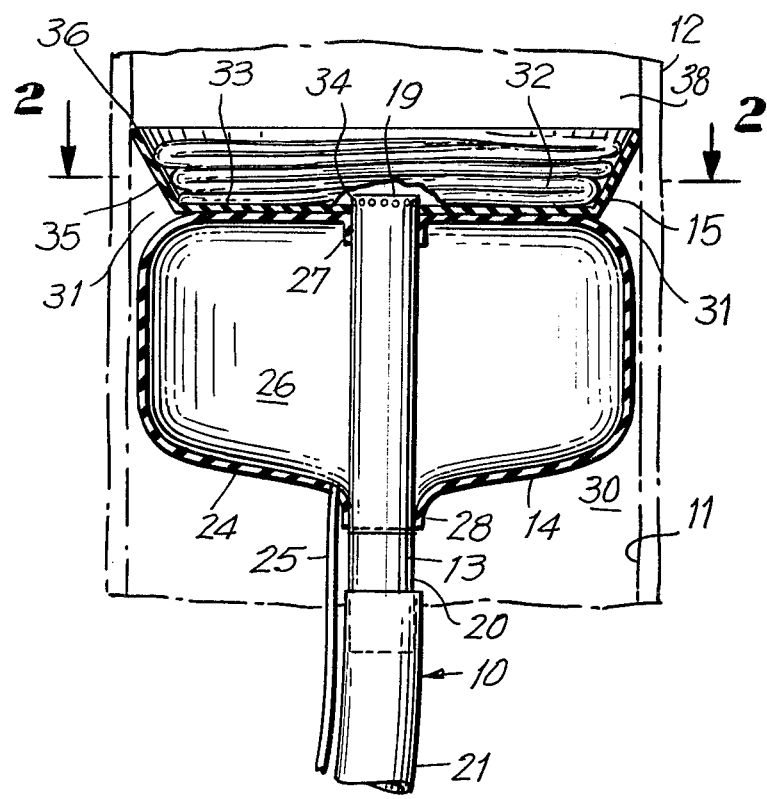
FIG. 1 is a fragmentary vertical sectional view of an embodiment of the invention in position within a surgical cavity in inflated condition.
Figure 2:
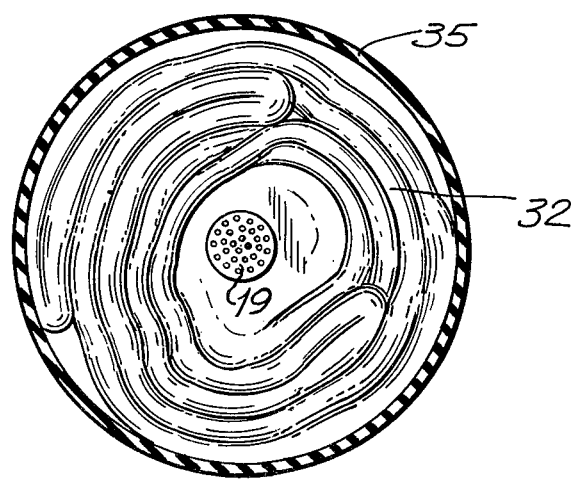
FIG. 2 is a top plan view thereof as seen from the plane 2—2 in FIG. 1.

In accordance with the invention, the device, generally indicated by reference character 10, is illustrated in FIG. 1 in the drawing in inflated condition within a surgical cavity 11 in the body 12 of a patient. It includes a generally centrally disposed rigid tube 13 surrounded by an inflatable element 14, and an upper generally cup-like support element 15.

The tube 13 may be of relatively inert metal or suitable synthetic resinous material, and includes an inner vented end covered by an orificed plate 19. The outer end 20 is provided with a drain tube 21 connected to a source of suction.

The inflatable element 14 is similar to that disclosed in my above-mentioned patent, and is of generally balloon-like configuration bounded by an outer surface 24. A separate inflating tube 25 extends along the tube 13 and communicates with the interior 26 of the inflated element. The element 14 is bonded to the outer surface of the tube 13 over an inner sealed area 27 and an outer sealed area 28, again as taught in my above-mentioned patent. In inflated condition, it contacts substantially the entire surface 30 of the surgical cavity 11, and the device is progressively deflated during the healing process. However, because it is practically impossible for the inflatable element to exactly conform to the cavity, particularly because of the absence of right angle edges, an annular interstice 31 is commonly formed into which portions of the lower bowel 32 can fall prior to the formation of adhesions with the normal contraction of the cavity.

To prevent this condition, the element 15 is provided. It includes a generally planar centrally disposed portion 33 having a central opening 34 surrounding the vented end 18 of the tube, as well as a peripheral portion 35 of arcuate configuration. The area 35 terminates in an edge 36 of a diameter at least as great as the largest possible transverse excursion of the inflatable element. The element 15 may be secured to the element 14 by bonding in the centrally disposed portion 33, to leave peripheral portion 35 independent thereof.

Referring to FIG. 1, after the inflatable element has been inflated, the edge 36 serves to seal the upper end 38 of the cavity, and support the lower portion of the bowel 39 from entry into any portion of the interstice 30 which extends substantially entirely around the periphery of the cavity.

In this manner, the bowel is maintained entirely clear of the area of the cavity, so that with the completion of the surgical procedure, the entire area of the cavity may be irradiated without fear of exposing any portion of the bowel.

I wish it to be understood that I do not consider the invention limited to the precise details of structure shown and set forth in this specification, for obvious modifications will occur to those skilled in the art to which the invention pertains.

I claim:

1. In an inflatable surgical packing for use in supporting the intestines of a patient following a hysterectomy or exenteration procedure, said packing having an inflatable element having an inner end surface, said inflatable element adapted to conform and substantially fill a surgical cavity formed by said procedure, said inflatable element having a principal axis and drainage means substantially aligned with said axis and projecting therethrough, the improvement comprising: an arcuate cupped support element lying generally transversely with respect to said axis and secured at a central area thereof to said inner end surface to surround said drainage means; said support element including a generally planar circular centrally disposed portion having a centrally positioned opening, said opening having an edge surrounding an open end of said drainage means, said portion being supported directly by said inflatable element, and a frusto-conical peripheral portion flaring in a direction away from said open end of said drainage means and having a free edge, said edge, when unstressed, extending outwardly of the maximum lateral excursion of said inflatable element, said open end of said drainage means being located within said frustoconical peripheral portion whereby upon the filling of said cavity by said inflatable element and the forming of an arcuate interstice at an inner peripheral end thereof with said cavity, said support element may overlie said interstice to be spread thereover by contact with otherwise unsupported intestinal tissue to overlie said interstice and prevent the pinching of such tissue.

* * * * *